(12) United States Patent
Waddell et al.

(10) Patent No.: US 9,025,303 B2
(45) Date of Patent: *May 5, 2015

(54) ION GENERATION DEVICE

(71) Applicant: Global Plasma Solutions, LLC, Savannah, GA (US)

(72) Inventors: Charles Houston Waddell, Roanoke, VA (US); Joseph Anton Christiansen, Savannah, GA (US)

(73) Assignee: Global Plasma Solutions, LLC, Savannah, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/021,507

(22) Filed: Sep. 9, 2013

(65) Prior Publication Data

US 2014/0078639 A1    Mar. 20, 2014

Related U.S. Application Data

(63) Continuation of application No. 12/578,753, filed on Oct. 14, 2009, now Pat. No. 8,564,924.

(51) Int. Cl.
*H01T 23/00*    (2006.01)
*B03C 3/41*     (2006.01)
*B03C 3/011*    (2006.01)

(52) U.S. Cl.
CPC . *B03C 3/41* (2013.01); *H01T 23/00* (2013.01); *B03C 3/011* (2013.01)
USPC ............................................................ 361/231

(58) Field of Classification Search
USPC ............................................................ 361/231
See application file for complete search history.

(56) References Cited

U.S. PATENT DOCUMENTS

| | | | |
|---|---|---|---|
| 4,757,422 A | 7/1988 | Bossard et al. | |
| 4,809,127 A | 2/1989 | Steinman et al. | |
| 5,741,352 A * | 4/1998 | Ford et al. | 96/68 |
| 6,680,033 B2 * | 1/2004 | Ishii | 422/306 |
| 6,850,403 B1 | 2/2005 | Gefter et al. | |
| 7,177,133 B2 | 2/2007 | Riskin | |
| 7,256,979 B2 | 8/2007 | Sekoguchi et al. | |
| 8,106,367 B2 | 1/2012 | Riskin | |

* cited by examiner

*Primary Examiner* — Stephen W Jackson
(74) *Attorney, Agent, or Firm* — Clements Bernard PLLC; Seth L. Hudson

(57) ABSTRACT

The present invention provides methods and systems for an ion generator device that includes a base, a first and second pair of spaced-apart, opposed sidewalls projecting from the base to collectively form an interior storage compartment and to define an upper edge, a top portion engaged to the upper edge, at least one high voltage wire extending from the device, and a power supply for providing a voltage to the high voltage wire for producing ions.

20 Claims, 7 Drawing Sheets

ION GENERATION DEVICE

CROSS REFERENCE TO RELATED PATENT APPLICATION

This application is a continuation-in-part of co-pending U.S. patent application Ser. No. 12/578,753 filed Oct. 14, 2009, and entitled "SYSTEMS AND METHODS OF AIR TREATMENT USING BIPOLAR IONIZATION," the contents of which are incorporated in full by reference herein.

FIELD OF THE INVENTION

The present invention relates generally to the field of air treatment, and more particularly to the treatment of air using bipolar ionization.

BACKGROUND OF THE INVENTION

Air and other fluids are commonly treated and delivered for a variety of applications. For example, in heating, ventilation and air-conditioning (HVAC) applications, air may be heated, cooled, humidified, dehumidified, filtered or otherwise treated for delivery into residential, commercial or other spaces.

Needs exist for improved systems and methods of treating and delivering air for these and other applications. It is to the provision of improved systems and methods meeting these needs that the present invention is primarily directed.

BRIEF SUMMARY OF THE INVENTION

According to an embodiment of the present invention, an ion generator device includes a base, a first and second pair of spaced-apart, opposed sidewalls projecting from the base to collectively form an interior storage compartment and to define an upper edge, a top portion engaged to the upper edge, at least one high voltage wire extending from the device, and a power supply for providing a voltage to the high voltage wire for producing ions.

According to another embodiment of the present invention, an ion generator device includes a base having an outer edge and the first and second pair of spaced-apart, opposed sidewalls projecting therefrom.

According to yet another embodiment of the present invention, an ion generator device includes a base having an outer edge and the first and second pair of spaced-apart, opposed sidewalls projecting therefrom.

According to yet another embodiment of the present invention, an ion generator device includes a transformer housed within the interior storage compartment and is engaged to the power supply and the at least one high voltage wire.

According to yet another embodiment of the present invention, an ion generator device includes two high voltage wires extending from the device, wherein one of the high voltage wires produces negative ions and the second high voltage wire produces positive ions.

According to yet another embodiment of the present invention, an ion generator device includes at least one bore within the top portion, whereby the at least one high voltage wire extends therethrough.

According to yet another embodiment of the present invention, an ion generator device includes a retention flange disposed on one of the sidewalls and extending therefrom.

According to yet another embodiment of the present invention, an ion generator device includes an LED light disposed on the top portion.

According to yet another embodiment of the present invention, an ion generator device includes a base that extends to an outer edge, a first and second pair of spaced-apart, opposed sidewalls projecting from the base to collectively form an interior storage compartment and to define an upper edge. The sidewalls each have an inner and outer sidewall surface and the second pair of opposed sidewalls intersect the first pair of opposed sidewalls to define corners. A top portion engaged to the upper edge, a first and a second high voltage wire extending from the device, and a power supply for providing a voltage to the high voltage wire for producing ions.

According to yet another embodiment of the present invention, an ion generator device includes a first brush engaged to the first high voltage wire and a second brush engaged to the second high voltage wire.

According to yet another embodiment of the present invention, an ion generator device includes a first brush engaged to the first high voltage wire and a second brush engaged to the second high voltage wire, wherein the first brush and second brush contain bristles composed of a thermoplastic impregnated with carbon.

According to yet another embodiment of the present invention, an ion generator device includes an interior cavity that includes an epoxy.

According to yet another embodiment of the present invention, an ion generator device includes a first bore and a second bore within the top portion, whereby the first high voltage wire extends through the first bore and the second high voltage wire extends through the second bore According to yet another embodiment of the present invention, an ion generator device includes a retention flange with a hollow bore disposed therein, the retention flange is engaged to the device.

According to yet another embodiment of the present invention, an ion generator device includes a circuit board including a transformer disposed within the interior storage compartment.

According to yet another embodiment of the present invention, a method of producing ions includes providing an ion generator device including a base, a first and second pair of spaced-apart, opposed sidewalls projecting from the base to collectively form an interior storage compartment and to define an upper edge, a top portion engaged to the upper edge, at least one high voltage wire extending from the device, a power supply for providing a voltage to the high voltage wire for producing ions; and placing the ion generator device within the housing of the air handler unit.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
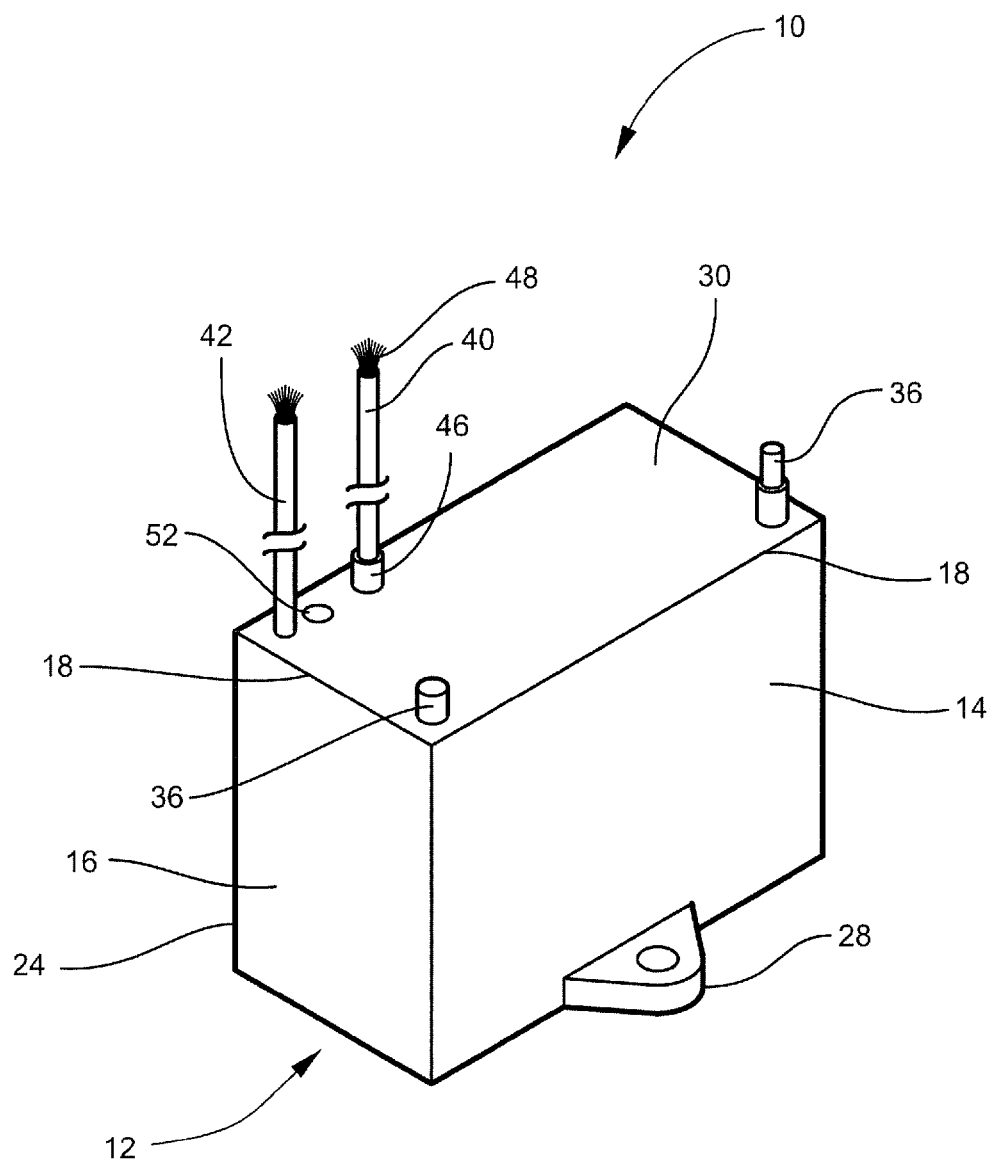
FIG. 1 is a perspective view of the device.
Figure 5:
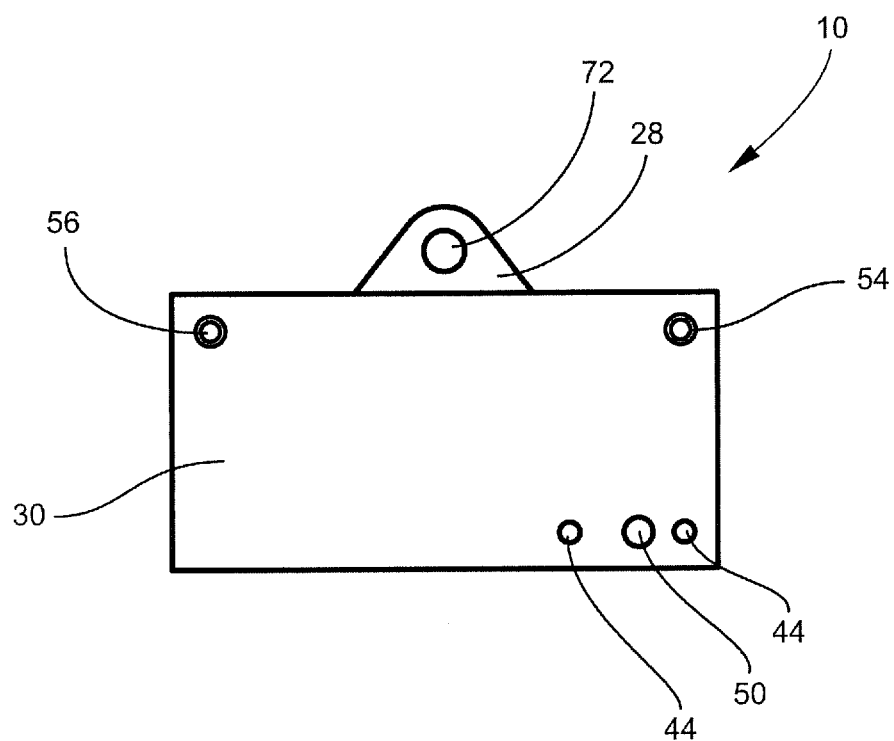
FIG. 5 is a top view of the device.
Figure 6:
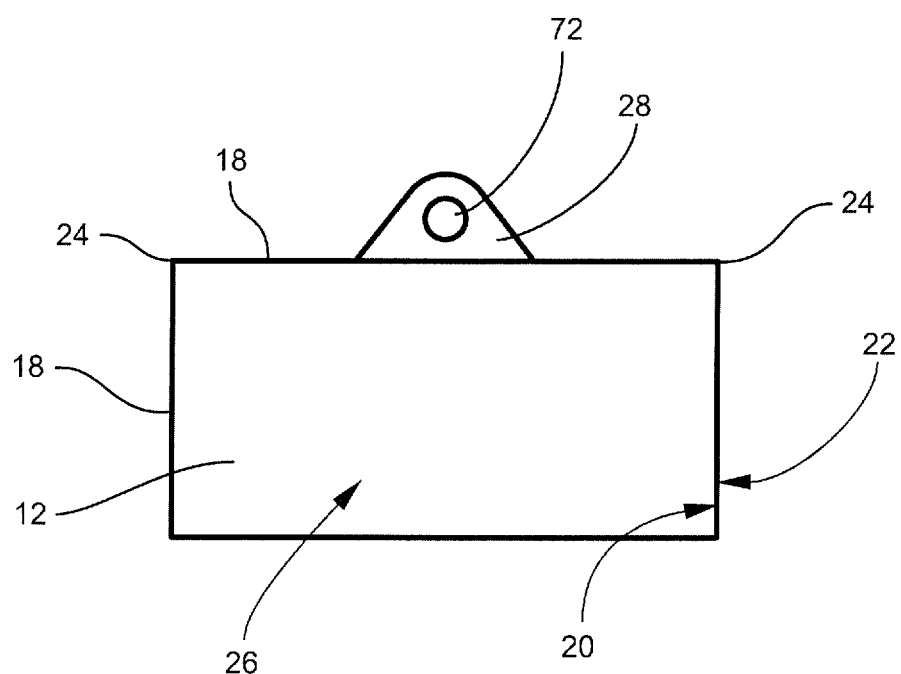
FIG. 6 is a top view of the sidewalls and base.

Referring now specifically to the drawings, and as illustrated in FIGS. 1, 5, and 6, the bipolar ionization device is shown generally at reference numeral 10. The device 10 includes a base 12 that extends to an outer edge. First and second pairs of opposed sidewalls 14, 16 extend from the outer edge of the base 12 to an upper edge 18. The sidewalls 14, 16 each have an inner and outer sidewall surfaces 20, 22. As shown in FIG. 6, each of the second pair of sidewalls 16 interconnects the first pair of sidewalls 14 to define corners 24 and an interior storage compartment 26. At lease one retention flange 28 extends from a first or second sidewall 14, 16 or the base 12. A top portion 30 is engaged above the interior storage compartment 26, and preferably on the upper edge of the first and second pairs of opposed sidewalls 14, 16, forming an enclosed interior storage compartment 26.

Figure 2:
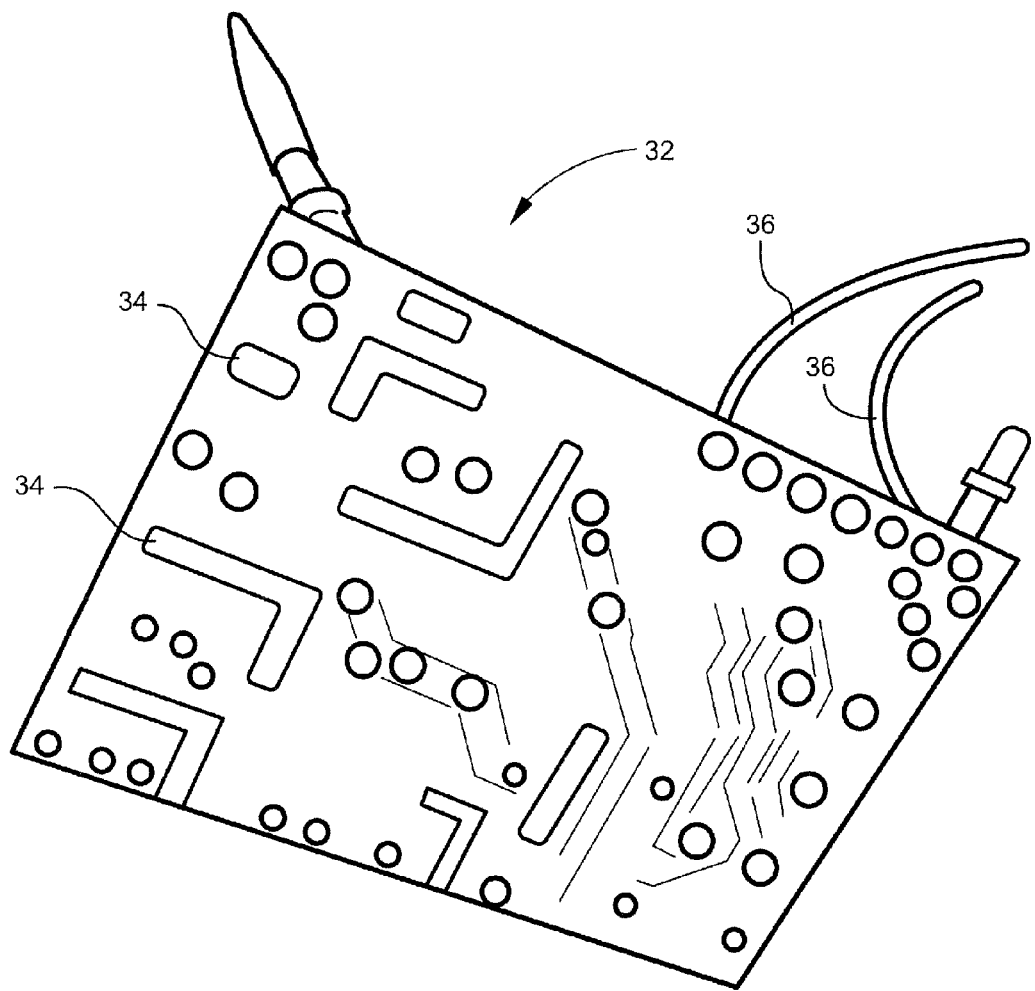
FIG. 2 is a perspective view of the circuit board within the device.
Figure 3:
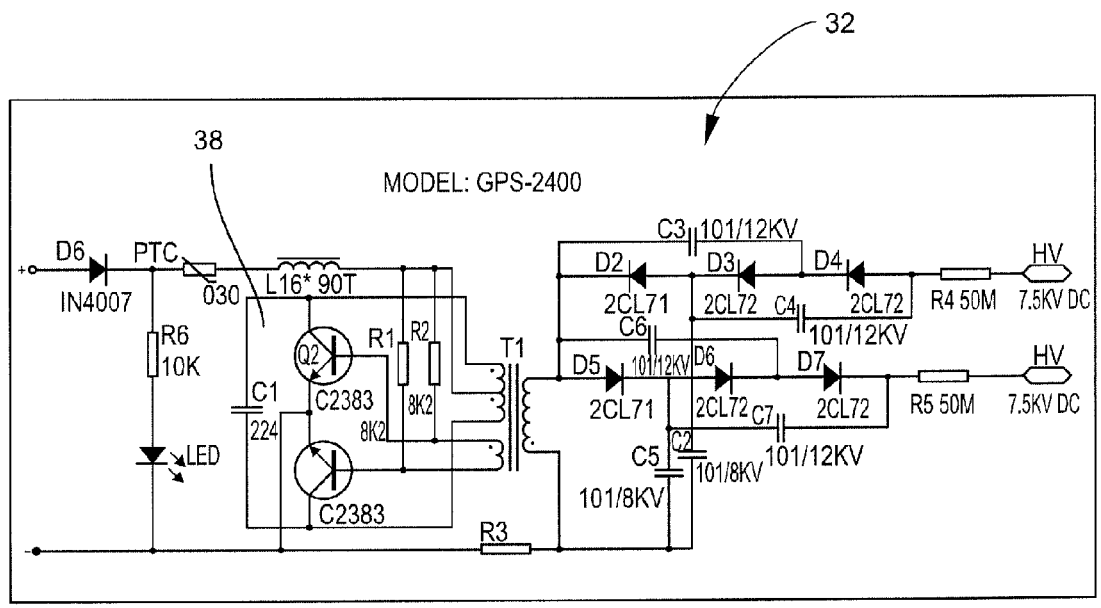
FIG. 3 is a circuit diagram of the device.

A circuit board 32, as illustrated in FIG. 2, is contained within the interior storage compartment 26, having a circuit diagram as shown in FIG. 3. The circuit board 32 is not continuous and has air gaps 34 contained therein. The purpose of the air gaps 34 is to prevent the high voltage from jumping to the low voltage area, and preventing the low voltage from jumping to the high voltage area. The interior storage compartment 26 may be filled with an epoxy. The circuit board 32 includes a power supply source 36, a transformer 38, and a first high voltage wire 40, and a second high voltage wire 42.

The top portion 30 of the device 10 contains at least two bores 44 that extend therethrough to the interior storage compartment 26. The first high voltage wire 40 extends through a bore 44 and the second high voltage wire 42 extends through another bore 44. In one embodiment, a hollow column 46 encircles the bore 44 and extends perpendicularly upward from the top portion 30 of the device 10 for providing support to the first or second high voltage wire (40,42). As illustrated, a hollow column 46 encircles the bore 44 containing the first high voltage wire 40, and a hollow column 46 encircles the bore 44 containing the second high voltage wire 40. The end of the first and second high voltage wire (40,42) contains a brush 48 that contains a plurality of bristles that extend outwardly away from the brush 48. The brush 48 and its bristles may be made of any material that conducts electricity. In one embodiment, the bristles of the brush 48 is composed of a thermoplastic polymer imbedded with conductive material that allows the polymer to conduct electricity. For example, the bristles of the brush 48 may be composed of polypropylene or polyethylene and impregnated with carbon. Generally, the bristles of the brush 48 may contain between about 20 to about 80 wt % polypropylene copolymer or polyethylene copolymer, between about 5 to about 40 wt % talc, and from about 5 to 40 wt % carbon black. However, any other resistive, inductive, reactive or conductive plastic or non-metallic material may be utilized for the bristles of the brush 48.

The brush 48 is engaged to the end of the high voltage wires 40,42. In one embodiment, the brush 48 is crimped to the end of the high voltage wires 40, 42 extending outwardly from the device 10. In another embodiment, the brush 48 is engaged to the end of the high voltage wires 40, 42 extending outwardly from the device 10 by heat shrink. The high voltage wires 40, 42 come off the transformer 38 at 6500 volts, wherein the first high voltage wire 40 and associated brush 48 deposits a stream of negative ions 68a into the surrounding air and the second high voltage wire 42 and associated brush 48 deposits positive ions 68b into the surrounding air.

The device 10 preferably produces approximately equal amounts of positive 68b and negative ions 68a, regardless of airflow velocity or other conditions such as humidity or temperature. In example forms, the device 10 produces positive ions 68b and negative ions 68a in a concentration of at least about $10^9$ ions/second, and operates on 24 VAC, 110 VAC or 200 VAC to 240 VAC without the use of an external transformer. In alternate embodiments, the device generates negative ions 68a only, or positive ions 68b only, or generate negative ions 68b and positive ions 68a in unequal quantities. The device 10 optionally utilizes nano-electronic components allowing the device to be very compact, requiring less than 1 watt/ion generator module, for example less than 0.5 watts/ion module, and in further examples less than 0.36 watts per ion module.

In one embodiment, the top portion 30 of the device 10 may contain an LED bore 50 that extends through the top portion 30 and into the interior storage compartment 26. An LED light 52 is positioned over the LED bore 50 and engaged to an LED wire that extends from the circuit board 32 to the LED light 52. When current is flowing through the high voltage wires 40, 42, current also flows through the LED wire and illuminates the LED light 52, indicating the device 10 is operating. The top portion 30 contains a first power supply bore 54 and a second power supply bore 56 for receiving the positive and negative power supply wires that serve as the power supply source 36.

Figure 4:
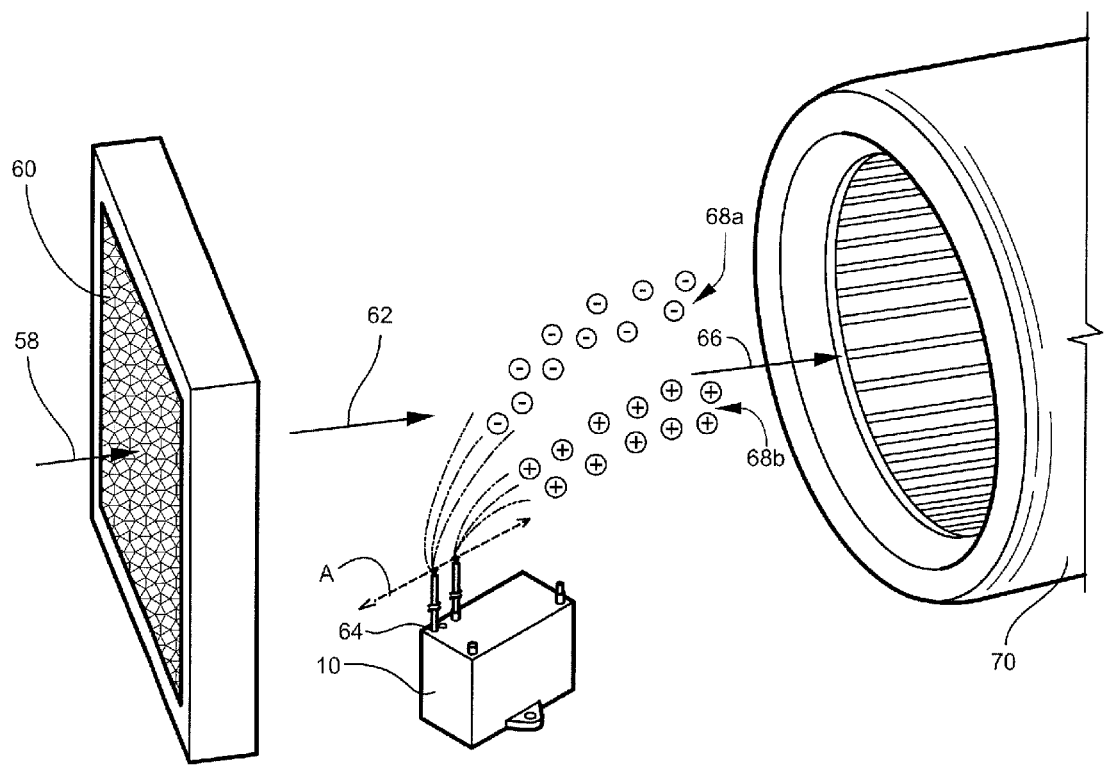
FIG. 4 is a perspective view of the device within an air handler.

FIG. 4 shows internal components of an individual air handler unit according to one embodiment of the invention. An inlet airflow 58 flowing through a conduit such as the housing of the air handler unit or a duct is filtered through a filter 60 such as a mesh, screen, paper, cloth or other filter media. A filtered airflow 62 downstream of the filter 60 is treated by discharge of bipolar ionization 64 from the device 10 to form an ionized airflow 66. The bipolar ionization 64 comprises a stream of negatively charged (−) ions 68a, and a stream of positively charged (+) ions 68b. The ionized airflow 66 enters the inlet of a fan or blower 70 for delivery to the treated air space, and is optionally heated or cooled by passing across or through a cooling coil or heating element. The coil, filter 60, device 10 and fan 70 are optionally mounted within a housing of the air handler unit. Example modes of attachment of the device 10 include, without limitation, adhesive, hook-and-loop fasteners, straps, screws, clips or other mechanical fasteners, magnetic mounting, and/or mounting brackets or carriers affixed to or through the housing or associated ductwork. The mode of attachment may be inserted through a bore 72 in the retention flange 28 for engaging the device 10 to the housing of an air handler unit.

The bipolar ion generator 38 is positioned and secured in place within the housing of the air handler unit such that the electrodes 40⁺ and 40⁻ are aligned generally perpendicularly to the direction of the airflow 34 across the ion generator, to prevent recombination of the positively charged ions with the negatively charged ions. In other words, a vector representing the average flow velocity of the airflow 34 is at approximately a right angle (90°) to an axis A extending between the electrodes 40⁺ and 40⁻. One or more ion generator(s) 38 can be installed within the housing of each air handler unit, as required to generate the desired level of ion delivery for a given airflow, as may be determined by the airflow rate (CFM) of the fan 44 and ion discharge rate of each ion generator. The ion generator(s) are preferably positioned generally centrally in relation to the airflow or evenly distributed across the airflow path. If more than one ion generator is provided in an air handler unit, they are sufficiently spaced and positioned relative to one another to minimize recombination of positive ions with negative ions.

The treatment of air by delivery of bipolar ionization to an airflow within a conduit according to the systems and methods of the present invention may be utilized for various purposes. For example, application of bipolar ionization to an airflow within an HVAC conduit such as an air handler housing or duct may be utilized to abate allergens, pathogens, odors, gases, volatile organic compounds, bacteria, virus, mold, dander, fungus, dust mites, animal and smoke odors, and/or static electricity in a treated air space to which the airflow is directed. Ionization of air in living and working spaces may reduce building related illness and improve indoor air quality; and additionally can reduce the quantity of outside air needed to be mixed with the treated indoor air, reducing heating and cooling costs by enabling a greater degree of air recirculation.

The base 12, first and second pair of sidewalls 14, 16, top portion 30, and retention flange 28 may be composed of a plastic. As illustrated, the first pair of sidewalls 14 is greater in width than the second pair of sidewalls 16. The retention flange 28 is positioned on one of the first pair of sidewalls 14. However, it should be noted that the retention flange 28 may be disposed on any of the sidewalls. Alternatively, two retention flanges 28 may be disposed on the sidewalls of the device 10. In another alternative embodiment, a plurality of retention flanges 28 may be disposed on the sidewalls.

Figure 7:
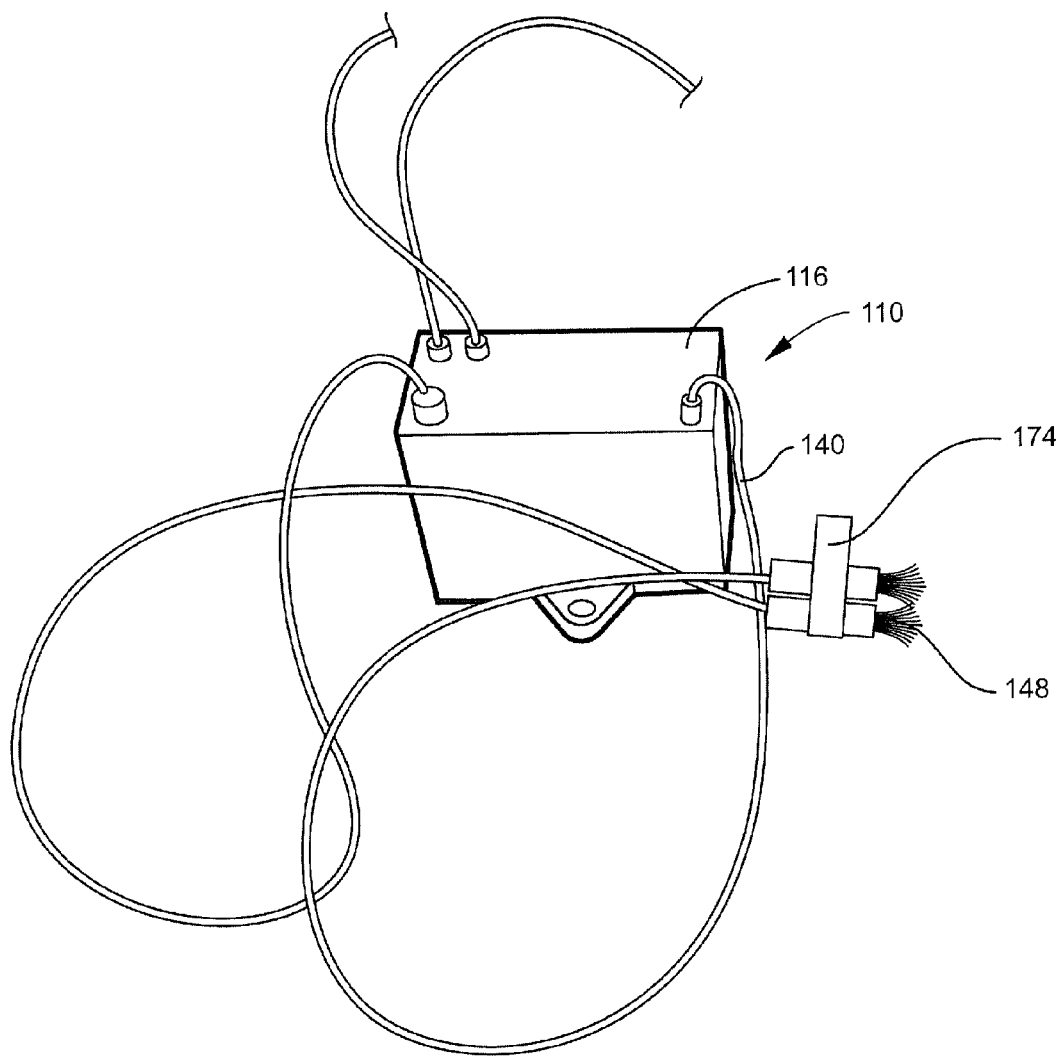
FIG. 7 is a perspective view of an alternative embodiment of the device.

An alternative embodiment of the device 110 is illustrated in FIG. 7. The device 110 contains a first and second elongate high voltage wire (140, 142). The first and second high voltage wire (140,142) contain a brush 148. The elongated first and second high voltage wire (140,142) are able to extend substantially away from the base 112 and sidewalls 114,116. The first and second high voltage wires (140,142) are preferably less than two feet in length, and more preferably are equal to or less than twelve inches long, and most preferably equal to or less than between twelve inches long and four inches long. The first and second high voltage wires (140, 142) contain a first end and a second end. The first end is engaged to the housing of the device 10 and the second end extends outward and contains the brush 148. A brush holder 174 is disposed on the second end.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An ion generator device, comprising:
a base,
a first and second pair of spaced-apart, opposed sidewalls projecting from the base to collectively form an interior storage compartment and to define an upper edge;
a top portion engaged to the upper edge;
at least one high voltage wire extending from the device;
a power supply for providing a voltage to the high voltage wire for producing ions.

2. The ion generator device of claim 1, further comprising a base having an outer edge and the first and second pair of spaced-apart, opposed sidewalls projecting therefrom.

3. The ion generator device of claim 1, further comprising a transformer housed within the interior storage compartment and is engaged to the power supply and the at least one high voltage wire.

4. The ion generator device of claim 1, further comprising two high voltage wires extending from the device, wherein one of the high voltage wires produces negative ions and the second high voltage wire produces positive ions.

5. The ion generator device of claim 1, further comprising at least one bore within the top portion, whereby the at least one high voltage wire extends therethrough.

6. The ion generator device of claim 1, further comprising a retention flange disposed on one of the sidewalls and extending therefrom.

7. The ion generator device of claim 1, further comprising an LED light disposed on the top portion.

8. An ion generator device, comprising:
a base that extends to an outer edge,
a first and second pair of spaced-apart, opposed sidewalls projecting from the base to collectively form an interior storage compartment and to define an upper edge, the sidewalls each have an inner and outer sidewall surface and the second pair of opposed sidewalls intersect the first pair of opposed sidewalls to define corners;
a top portion engaged to the upper edge;
a first and a second high voltage wire extending from the device;
a power supply for providing a voltage to the high voltage wire for producing ions.

9. The ion generator of claim 8, further comprising a first brush engaged to the first high voltage wire and a second brush engaged to the second high voltage wire.

10. The ion generator of claim 8, further comprising a first brush engaged to the first high voltage wire and a second brush engaged to the second high voltage wire, wherein the first brush and second brush contain bristles composed of a thermoplastic impregnated with carbon.

11. The ion generator of claim 8, wherein the interior cavity includes an epoxy.

12. The ion generator of claim 8, wherein one of the high voltage wires produces negative ions and the second high voltage wire produces positive ions.

13. The ion generator device of claim 8, further comprising a first bore and a second bore within the top portion, whereby first high voltage wire extends through the first bore and the second high voltage wire extends through the second bore.

14. The ion generator device of claim 8, further comprising a retention flange with a hollow bore disposed therein, the retention flange is engaged to the device.

15. The ion generator device of claim 8, further comprising an LED light disposed on the device.

16. The ion generator device of claim 8, further comprising a circuit board including a transformer disposed within the interior storage compartment.

17. A method of producing ions, comprising:
providing an ion generator device including a base, a first and second pair of spaced-apart, opposed sidewalls projecting from the base to collectively form an interior storage compartment and to define an upper edge, a top portion engaged to the upper edge, at least one high voltage wire extending from the device, a power supply for providing a voltage to the high voltage wire for producing ions; and
placing the ion generator device within the housing of the air handler unit.

18. The method of producing ions according to claim 17, further comprising an ion generation device including two high voltage wires extending from the device, wherein one of the high voltage wires produces negative ions and the second high voltage wire produces positive ions.

19. The method of producing ions according to claim 17, further comprising an ion generation device including a brush with bristles composed of a thermoplastic impregnated with a carbon engaged to the at least on high voltage wire.

20. The method of producing ions according to claim 17, further comprising an ion generation device including a retention flange with a hollow bore disposed therein, the retention flange is engaged to the device.

\* \* \* \* \*